United States Patent [19]

Urso

[11] Patent Number: 4,960,103
[45] Date of Patent: Oct. 2, 1990

[54] VERSATILE HEATER/COOLER

[76] Inventor: Charles L. Urso, 215 Newton St., Waltham, Mass. 02154

[21] Appl. No.: 373,462

[22] Filed: Jun. 30, 1989

Related U.S. Application Data

[63] Continuation-in-part of Ser. No. 212,505, Jun. 28, 1988, Pat. No. 4,898,148.

[51] Int. Cl.[5] .................................................. A61F 7/00
[52] U.S. Cl. ...................................... 126/204; 126/208; 126/266; 126/367; 128/402
[58] Field of Search ............... 126/5, 43, 44, 204–210, 126/367, 266, 389; 128/399, 400, 402; 312/1

[56] References Cited

U.S. PATENT DOCUMENTS

| | | | |
|---|---|---|---|
| 404,572 | 6/1889 | Spiro | 126/367 |
| 506,810 | 10/1893 | Cardarelli | 126/367 |
| 648,032 | 4/1900 | Janesch | 126/367 |
| 971,735 | 10/1910 | Edwards | 126/266 |
| 1,468,561 | 9/1923 | Friend | 126/367 |
| 1,754,971 | 4/1930 | Waigand | 128/402 |
| 3,220,424 | 11/1965 | Nelson | 128/402 |
| 3,811,559 | 5/1974 | Carter | 126/266 |
| 4,329,997 | 5/1982 | de Yampert et al. | 126/402 |
| 4,331,254 | 5/1982 | Haggerty | 312/1 |
| 4,497,313 | 2/1985 | Kurosawa | 128/400 |
| 4,691,688 | 9/1987 | Urso | 126/204 |
| 4,896,655 | 1/1990 | Urso | 126/59 |
| 4,898,148 | 2/1990 | Urso | 126/204 |

FOREIGN PATENT DOCUMENTS 2613 7/1909 United Kingdom ................ 126/367

Primary Examiner—James C. Young
Attorney, Agent, or Firm—Hamilton, Brook, Smith & Reynolds

[57] ABSTRACT

A versatile heater/cooler (2) comprising a chest (4) having insulated walls (6, 8, 10, 12, 14) including a lid (10). Contained within the chest is a removable heating and cooling source (46) which is submersible in a liquid for heating or cooling the latter. The source comprises first and second vertical conduits (48, 50) having lower portions connected for fluid communication with a transverse body (52) which forms a combustion chamber. The chamber serves for burning fuel (80) or for containing a refrigerant introduced by way of the conduits. Included in the chest lid is a vent port (110) for venting the chest contents including the source, and two limb ports (18, 20) for inserting the limbs of a user through the ports and into the interior of the chest. A self-adjusting shield (22, 24) connected to an edge portion of each limb port, yieldingly surrounds each limb for preventing hot or cold air losses from the chest. The invention also includes movable carrying handles (126, 128) which, in an erect position, form a frame which supports various user aids for special applications of the invention.

11 Claims, 9 Drawing Sheets

VERSATILE HEATER/COOLER

RELATED APPLICATION

This application is a continuation-in-part of U.S. patent application Ser. No. 212,505, filed June 28, 1988, now U.S. Pat. No. 4,898,148.

TECHNICAL FIELD

This invention relates to insulated enclosures for maintaining a temperature condition and more particularly to insulated enclosures having self-contained submersible heating means.

BACKGROUND

When we leave the comforts of home to experience the great outdoors, we leave the important benefits of home fixtures and appliances. Among the most needed of the home devices are those that maintain water at high and low temperatures and those that contain the desired water for its various uses. This may involve a water heater, a refrigerator, a sink and a tub. To bring along existing portable substitutes for such devices is impractical since together they would constitute too large a load for most family cars.

Dish Washing and Bathing

Portable means for dish washing and for personal bathing often requires a multi-gallon pot, a portable stove, and a plastic tub; a bulky combination. A more compact combination is needed.

First Aid

The fast application of wet heat or cold is useful in the treatment of some types of injuries which are apt to occur in outdoor environments. Conventional portable devices for providing the treatment would include an insulated cooler, a large pot, a portable stove, and a large basin or pan. An all-in-one combination would be a great benefit.

Heating and Cooling the Body

Because of poor blood circulation, elderly people are in need of a means for heating or cooling their bodies when outdoor temperatures are insufficient or excessive. Small children are also very vulnerable to discomfort and injury from temperature extremes. A convenient portable combination heater and cooler is needed for heating or cooling a person's body to help avoid heat stroke, heat exhaustion, hyperthermy, hypothermy, and frostbite. Such an apparatus could serve as a "safety net" for the elderly and children in changing weather conditions. Others who could benefit are fishermen, miners, farm workers, construction workers, campers, boat operators, athletes, and other sportsmen.

Heating Food

Heating food when there is no kitchen is available, especially food in quantity, generally requires bulky equipment including a portable stove or heater and large pots or pans.

It would be desirable, therefore, to provide a compact apparatus that could be safely used for all of the abovementioned needs, including dish washing, bathing, first aid treatments, body heating and cooling, and food heating and cooling.

SUMMARY OF THE INVENTION

The present invention provides a compact apparatus for:

washing dishes, utensils and other camping equipment wherein the apparatus includes a self-contained submersible heating device to heat water in a tub-like receptacle for immersing the articles to be washed;

personal bathing having the features described above wherein a user can stand in the tub-like receptacle;

cooling food or heating food in sufficient quantity to be suitable for catering, especially in conditions where there is minimal equipment and no kitchen;

first aid and other medical applications having means for keeping water hot or cold, and including a receptacle for receiving and treating some types of injuries and afflictions to limbs; and heating or cooling the body of the user.

Other objects and advantages will become apparent from consideration of the drawings and ensuing description which includes a list of more specific uses and applications.

BRIEF DESCRIPTION OF THE DRAWINGS

The accompanying drawings in combination with the description herewith, illustrate features and advantages of the invention. Like reference characters in different views refer to the same parts. The drawings are intended to illustrate principles of the invention and are not necessarily to scale and in which drawings.

DETAILED DESCRIPTION

Figure 1:
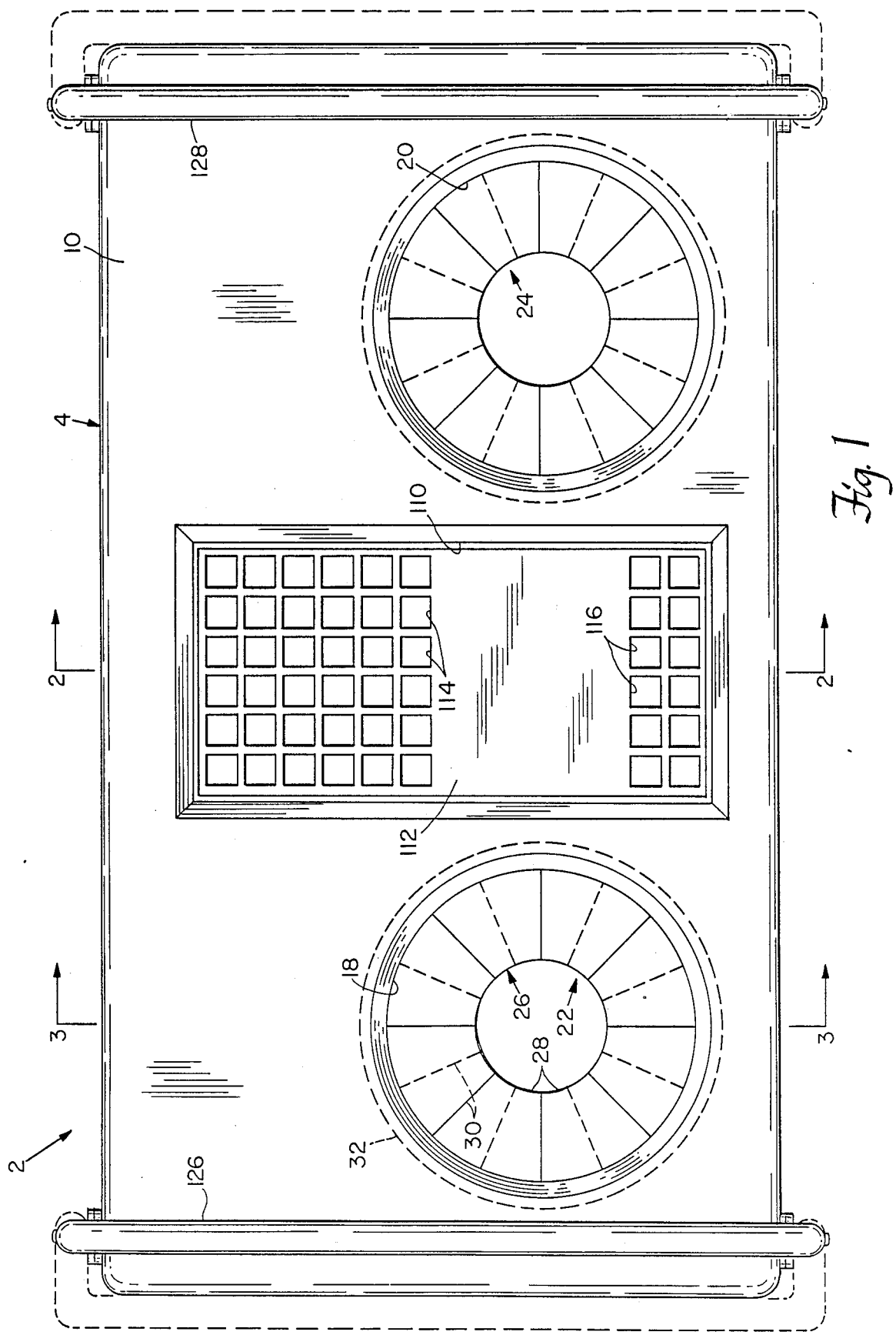
FIG. 1 is a top view of an apparatus in accordance with the invention in proper orientation for limb insertion wherein the limb port covers are removed and the vent port cover is removed.

A first embodiment of the invention which can serve as either a heater or cooler (referred to herein as a versatile heater/cooler) is indicated generally by reference numeral 2 in FIG. 1. The invention comprises a six-sided container or chest 4 (FIG. 1 and 2) having walls 6, 8, 10, 12, 14 defining a hollow interior. The walls include conventional insulating means for inhibiting heat transfer through the walls. Details of the internal construction of the walls are generally not shown since the construction methods are well-known in the art. A conventional double-wall construction may be used, for example, wherein the inner wall element may be aluminum or a plastic sufficiently heat resistant to contain hot water in the chest. Each of the chest walls may otherwise be of a single-wall construction comprising a rigid, heat resistant, foam plastic. The minute cells in the foam provide the insulating quality.

Figures 6, 7:
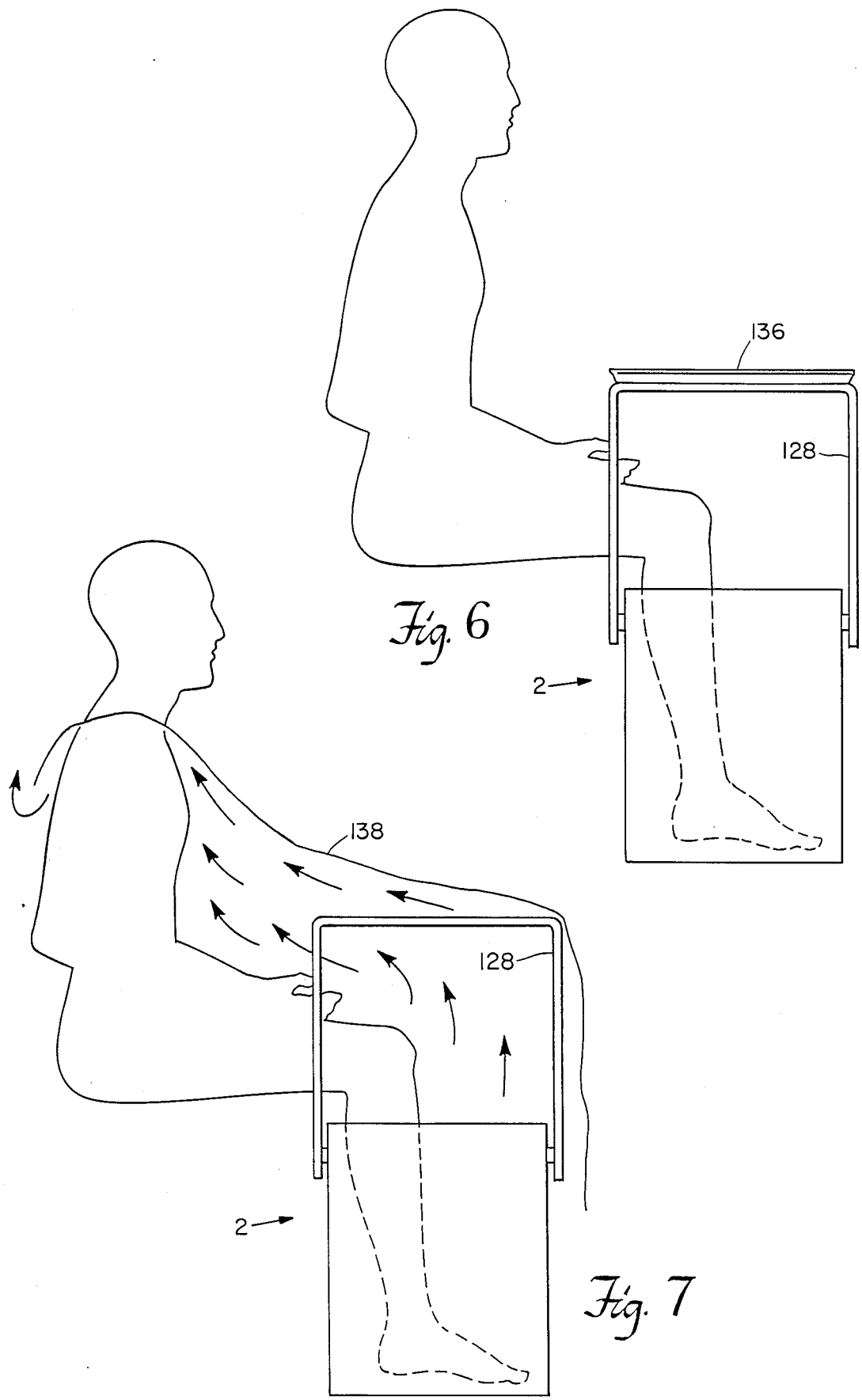
FIG. 6 is a diagrammatic view of a seated user having at least one leg inserted through a limb port and into the chest, wherein the carrying handles are in an upright position for supporting a tray.
FIG. 7 is a diagrammatic view of a seated user having his legs inserted into the chest wherein a blanket covers the user and forms a canopy over the upright carrying handles to entrap heated air rising from the vent port thereby enveloping the user.

Wall 10 serves as a removable lid which includes portions defining limb ports 18, 20 (FIG. 1). The port size is suitable for insertion of a limb through each port and into the interior of the chest (FIG. 6 and 7). Alignment of the two ports is parallel with the longitudinal axis of the lid so that two limbs of a user can conveniently be simultaneously inserted in the chest. Hence, a seated user can insert both lower legs into the chest, one leg in each respective port. The edge portion of each port being curved or annular to comfortably surround the limb.

Figure 3:
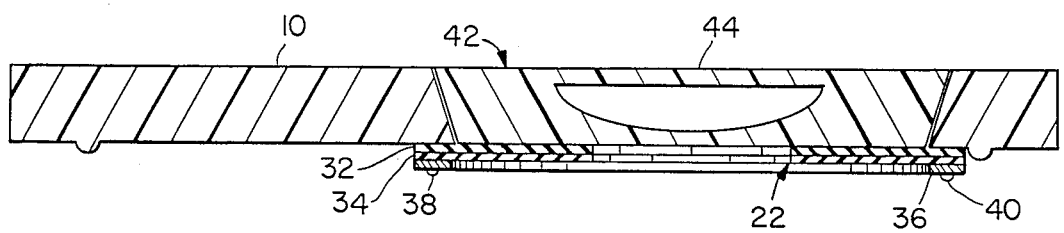
FIG. 3 is a cross-sectional view of the chest lid taken along the line 3—3 of FIG. 1, but including a limb port cover.

Connected to an underside of each port edge portion is a self-adjusting shield 22, 24, respectively, such that each shield is concentric with a port (FIG. 1 and 3). Referring to shield 22, the same includes a corolla 26 having a plurality of resilient petals 28. The petals are formed by equidistant radial cuts 30 through each of two doughnut-shaped rubber sheets 32, 34, one sheet lying over the other. Each radial cut begins at the aperture or inside edge of a sheet and extends radially outward to end just below the edge of port 18. Each sheet is larger in diameter than a port diameter so that each petal includes an outer portion attached to a peripheral portion of a sheet. The cuts in sheet 32 (indicated by solid lines in FIG. 1) are located approximately midway between the cuts in sheet 34 (indicated by broken lines). Hence, the corolla petals overlap each other to resist the formation of open spaces between adjacent petals as they bend and spread.

Shield 22 is sandwiched between the edge portion of port 18 and an aluminum ring 36 fastened to the lid 10 by rivets 38, 40. The rivets pass through the ring and the shield, thereby connecting the shield to the port edge portion.

Shield 24 is constructed and mounted in the same manner as shield 22. The corolla petals of a shield are positioned to surround a limb passing through the associated port such that the petals yieldingly contact the limb thereby resisting the passage of air through the port. Thus, by minimizing any exchange of air between the interior and the exterior of the chest 4, the shields help to preserve a temperature condition in the interior of the chest.

When limb port 18 is not in use, it is closed by a removable limb port cover 42 (FIG. 3) which includes a handle 44 positioned in an annular recess in the cover. The cover is insulated and closely fitted to the port to avoid heat transfer through the idle port. A similar cover (not shown) closes port 20 when the latter is not in use.

Figure 2:
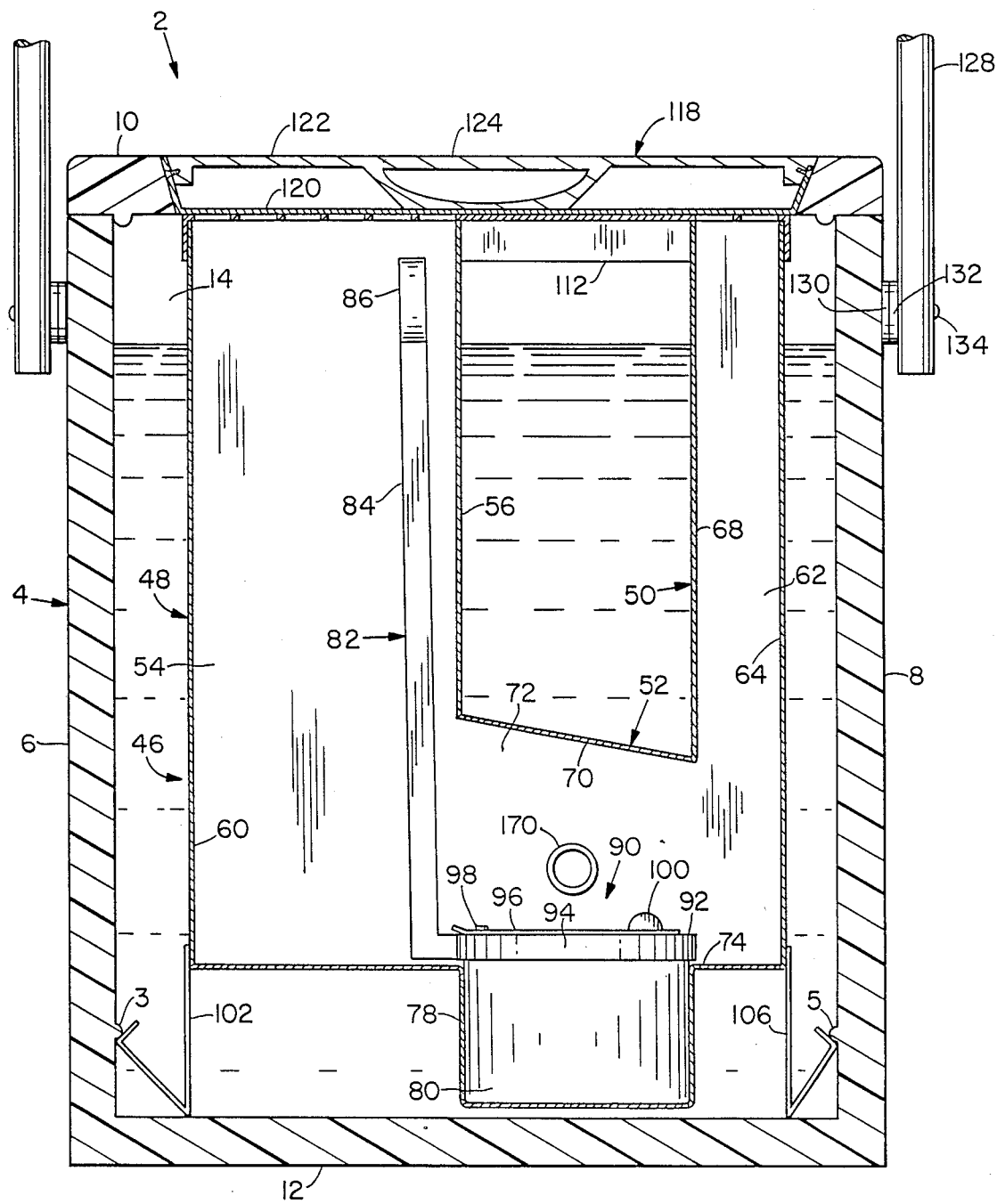
FIG. 2 is a cross-sectional view taken along the line 2—2 of FIG. 1, but including the vent port cover.
Figure 4:
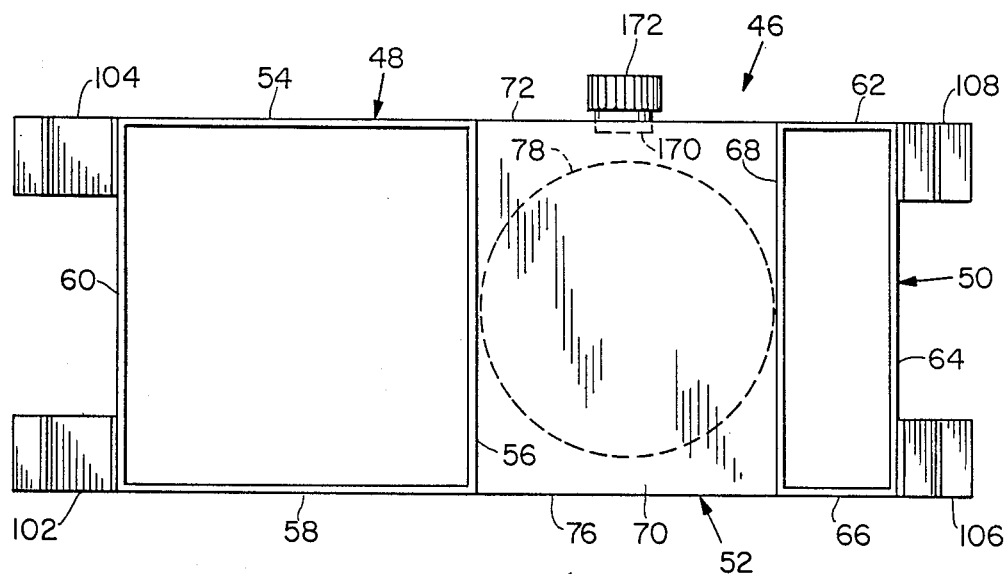
FIG. 4 is an isolated top view of the submersible heating and cooling source without the grate cap.

Within the chest 4 is a submersible heating and cooling source or H/C source 46 (FIG. 2 and 4). The H/C source comprises a first conduit 48 normally positioned vertically. Conduit 48 includes upper and lower portions wherein the upper portion is open for fluid communication between the hollow interior of the conduit and the outside atmosphere. Also included is a second conduit 50 normally positioned vertically. Conduit 50 includes upper and lower portions wherein the upper portion is open for fluid communication between the hollow interior of the conduit and the outside atmosphere.

A transverse body 52 forms a combustion chamber and is connected with the lower portion of the first conduit 48 wherein the combination forms a first passage between conduit 48 and the body. Thus, allowing fluid communication between the chamber and the first conduit interior. The body 52 is also connected with the lower portion of the second conduit 50 wherein the combination forms a second passage between conduit 50 and the body. Thus, allowing fluid communication between the chamber and the second conduit interior. The combination also allows the conduit interiors to be in fluid communication with each other.

As shown in the figures, conduit 48 includes vertical walls 54, 56, 58, and 60. Conduit 50 includes vertical walls 62, 64, 66, and 68. Transverse body 52 includes a sloped wall or roof 70, a horizontal wall or floor 74, and vertical walls 72, 76.

As can be seen in FIG. 2, the height of the roof above the floor at the first passage (formed at the joint of body 52 with conduit 48) is relatively higher than the height of the roof at the second passage (formed at the joint of body 52 with conduit 50). Thus, the height of the chamber, between the floor and the roof, increases as the distance toward the first conduit decreases. The first passage therefore enables convenient entry of a fuel source, by way of the first conduit and chamber, into a well described hereinafter.

The combination including the conduits and the chamber may be constructed from sheet metal by ordinary shop methods.

Extending downwardly from the body 52 is a cup-shaped fuel well 78. Access to the interior of the well 78 is through an annular entry in floor 74. Thus, the well is in fluid communication with the conduits 48, 50.

Received in the fuel well is a can 80 containing semi-solid fuel of the type commonly used in portable stoves and for heating chafing dishes. Cans containing the fuel are commercially available in several different sizes.

Figure 5:
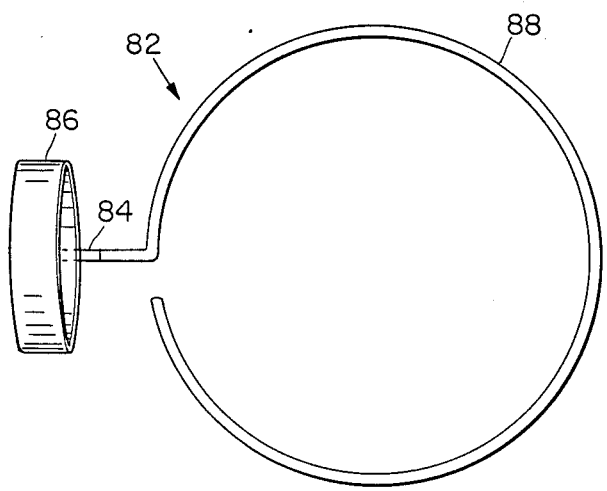
FIG. 5 is an enlarged top view of the fuel holding arm.

Fuel can 80 is placed and removed in the well 78 by means of a fuel holding arm 82 (FIG. 2 and 5). Arm 82 comprises an L-shaped shaft 84 having an upper end portion connected to a ring-shaped handle 86. Shaft 84 also includes a lower end portion which is connected to a ring-shaped holder 88 for surrounding and holding the fuel can 80. The holder 88 is sufficiently resilient so as to embrace the can under spring tension. A protruding annular top edge of the can prevents the latter from sliding through the holder. The fuel holding arm 82 can be formed by bending a single strip of metal into the described shape.

By holding the handle 86, a user can pass the arm 82 and fuel can 80 through the first conduit 48 for placement or removal of the can. The inner corners of conduit 48 provide ample room for arm 82 as the fuel can is lowered or raised in the conduit.

The sloping roof helps to guide the fuel can 80 to the entrance of the fuel well 78.

Positioned over the fuel can 80 and around the holder 88 is a flame attenuator 90. The attenuator 90 includes a cap portion 92 which resembles the lid of a jar. Cap 92 covers the fuel can while a rim portion 94 of the cap encircles the holder 88. A vertical slot (not shown) in the rim 94 receives the lower end portion of the shaft 84 so that the cap is able fit around the holder. The cap 92 includes a central annular aperture (not shown) through which a flame from the fuel can 80 passes through the attenuator. Also included is an annular plate 96 pivotally connected to the cap by a rivet 98. The plate is larger in diameter than the cap aperture and includes a small handle 100 so that a user can slide the plate over the aperture. Thus, the plate can be used to control the flame size by adjusting the amount by which the cap aperture is covered by the plate. The attenuator operates in a manner similar to conventional flame attenuators for other uses of semi-solid fuel, such as under chafing dishes.

Referring to FIG. 2 and 4, wall 72 of the transverse body 52 includes an aperture which receives a short pipe nipple 170. The nipple is press-fitted or welded therein to define a lighting port for igniting the fuel. A match can be passed through the lighting port to ignite the fuel.

The portion of the nipple 170 protruding from the outside of the wall 72 is threaded to mate with a threaded lighting port cap 172. By screwing the cap 172 over the nipple, the cap forms a fluid tight seal over the port.

All joints connecting the combination, which includes the conduits 48, 50, transverse body 52 and fuel well 78, are welded or brazed so that the combination below the conduit openings is fluid tight.

Welded to lower corners of the H/C source 46 are four resilient anchoring legs 102, 104, 106, and 108. Each leg is formed from a strip of resilient metal. When the H/C source is placed in the chest 4, a distal portion of each leg snaps under a horizontal bead 3, 5 (FIG. 2) protruding from a respective chest wall 6, 8. This arrangement provides legs for the H/C source and means for holding the latter down when the chest is filled with water or other liquid. Hence, the H/C source is prevented from floating. A user removes the H/C source from the chest by pulling the device up, thereby overcoming the spring resistance of the legs which can snap over the beads in either direction (up or down). Guides (not shown) on the chest walls can be used to guide the H/C source to a central portion of the chest interior.

The lid 10 includes a centrally positioned vent port 110 which is a rectangular opening directly above the H/C source 46 for ventilation of the latter (FIG. 1). A perforated grate cap 112 is placed over the openings of both conduits to prevent small objects from falling into the H/C source. Perforations 114 are positioned over the first conduit opening while perforations 116 are positioned over the second conduit opening (FIG. 1 and 2).

The lid 10 also includes a vent port cover 118 (FIG. 2) comprising a shallow rectangular metal pan 120 having a bottom wall and four side walls arranged to fit tightly into the vent port. The pan side walls are fixed to a molded plastic upper portion 122 of the cover 118 by means of screws. A handle 124 is positioned in an annular recessed portion of the molded plastic. Thus, the vent cover 118 is double-walled with an insulating void therebetween.

Referring to FIG. 2, the metal portion of cover 118 meets flush with grate cap 112 so that all the grate perforations are completely covered. It can be seen, therefore, that vent cover 118 can serve to shut off the H/C source. That is, the H/C source can only operate when the vent cover is removed since placement of the cover 118 in the vent port completely prevents any gases from entering or leaving the H/C source. The vent cover also serves to prevent the semi-solid fuel from drying out when the fuel can cover is removed. Hence, when the vent cover is in place, the fuel will not evaporate. Of course, the vent cover also helps to keep the contents of the chest hot or cold.

The heater/cooler 2 includes a U-shaped carrying handle 126, 128 pivotally mounted at each end portion of the chest (FIG. 1, 2, 6 and 7). Tightly sandwiched between each handle leg and a chest wall, is a spacer 130 (FIG. 2) juxtaposed with a rubber washer 132. A rivet 134 passes through the handle leg, the washer and spacer, and into the chest wall 8 to pivotally connect the combination. Friction, resulting from the tightly compressed rubber washer associated with each handle leg, maintains the handles in the position in which they are placed by a user. The handles may be moved, however, between an upper or erect position (indicated by the solid line representation in FIG. 1) and a lower position (indicated by the broken line representation) clear of the lid 10. Various uses of the handles will be explained in other sections of this specification.

A conventional drain plug (not shown) may be included in the chest for draining the latter of water or other liquid.

The chest lid 10 may also include conventional latches for holding the vent port cover and limb port covers in place in the lid. The latches would allow the lid to be removed and placed in any position without losing the port covers.

Operation of the Submersible H/C Source

Grate cap 112 is first removed in order to place a fuel can in the H/C source. By using arm 82, the fuel and the attenuator are positioned in the fuel well as shown in FIG. 2. As mentioned, the inside corners of first conduit 48 provide ample room for the arm as the latter is lowered into the conduit. Grate cap 112 can then be replaced on the H/C source wherein the lighting port cap 172 can be removed and the fuel ignited by way of the lighting port. After the fuel is ignited, the lighting port cap can be replaced and the H/C source can be immersed in liquid contained by the chest 4.

Alternatively, the fuel may be ignited outside of the H/C source while being held with a fuel holding arm. An advantage of the latter method of igniting the fuel, is that the H/C source does not have to be removed from the chest.

The flame heats roof 70 and other walls of the H/C source to transfer heat to the water or other liquid in which the H/C source is immersed. Heat from the fuel is transferred through the well to the water.

The roof 70 of the combustion chamber is sloped upward to direct rising combustion gases to the first conduit 48 so that the latter functions as a flue. Second conduit 50 functions to conduct atmospheric air to the chamber for supporting combustion.

With the flame source being well protected in the H/C source and chest, the operating heat/cooler can be left unattended to heat water and/or food in the chest. Users are free to enjoy outdoor activities.

The described combination provides a highly efficient system for heating a large volume of liquid, since there is very little heat loss. As mentioned, the H/C source can be shut off by replacing the vent port cover 118. The cover extinguishes the flame and prevents evaporation of the semi-solid fuel. It also keeps the heated liquid hot.

H/C source 46 also functions to contain a refrigerant, such as dry ice or ice cubes, introduced by way of the conduits so that the contents of the insulated chest 4 can be kept cold. Filling the H/C source with water and freezing it is another method of providing a refrigerant.

SPECIFIC USES OF THE INVENTION

For Dish Washing

After heating water in the chest 4 as described above, the lid 10 and H/C source 46 may be removed so that the open chest can serve as a water-filled tub or sink. Dishes, pots, pans, and other equipment may be immersed in the chest for washing at campsites and other remote locations.

For Bathing

Just as for dish washing described above, the open chest with its hot water can be used as a sink for personal washing. A user can also stand in the chest while taking a sponge bath. A child could sit in the chest water and thus use it as a tub.

For Heating or Cooling Food

With water contained in the chest, food contained in crocks, jars, cans and pots can be immersed in the chest water in order to heat the food. Lid 10 is kept closed during the heating process. The hot water can later be used for washing.

Instead of water, the chest can be filled with "uncontained" soup or chowder wherein the chest serves as the container. The H/C source 46 can then be immersed in the soup or chowder for heating. In this manner, other liquid foods including those having suspended solids can be heated. For these applications the submersible H/C source and the inner walls of the chest can be made from nontoxic metal, such as aluminum or stainless steel.

Hence, the invention is ideal for catering clambakes and outings with minimal equipment. The H/C source 46 can be in operation while on route to a function so that hot food can be served upon arrival. A low flame setting, in concert with the insulated chest, can keep food hot all day in the case of a full-day outing.

For cooling food or drinks in the chest, the H/C source 46 can be filled with a refrigerant as described above.

Heating and Cooling the Body

Blood continuously circulates through the skin of each limb wherein a considerable amount of heat is exchanged with the exterior environment. The same blood that passes through the limbs also travels throughout all the body vessels in continuous cycles. Therefore, if limbs are immersed in hot or cold water in the heater/cooler, the whole body will receive or lose heat (depending on whether the water temperature is above or below normal body temperature).

Hence, by having cold water in the chest 4 and both legs in the limb ports, an overheated person will cool his entire body. He could be seated in the same manner as the person indicated in FIG. 6. The heater/cooler would be very useful, for example, at outdoor events for the elderly or at athletic events. The invention can help avoid heat stroke or heat exhaustion.

As mentioned, hot water in the chest 4 can keep a user's entire body warm. A user will not burn his feet by contact with the operating H/C source because the water absorbs the heat. However, if the water becomes too warm the H/C source can be shut off or removed from the chest. Referring to FIG. 7, a sitting user can also cover himself and the upright handles with a blanket 138. The handles form a canopy frame wherein the blanket becomes a canopy for entrapping heated air (indicated by arrows) from the vent port (the vent port cover is removed). The heated air envelops the user for additional warmth. For added safety, the H/C source 46 could be shut off or removed after the water is heated. The hot air under the blanket would then be derived from the hot water.

The invention would be advantageous, therefore, in an emergency or simply as a means to keep warm or cool.

In the above applications of the invention, the user can wear disposable plastic coverings (such as those used by hospital personal) over his legs to avoid getting wet. This can also be done in some of the medical uses of the heater/cooler.

For First Aid and Other Medical Uses

When the H/C source 46 is filled with ice cubes, water in the chest can be kept cold. Alternatively, with the H/C source burning fuel, the chest water can be kept hot as long as desired. Thus, wet cold or wet heat treatments can be provided by inserting one or two arms or legs through the limb ports. Medications can be added to the water when appropriate.

Immersion, rather than wet pad applications, is preferred in some types of injuries or afflictions to a limb. The buoyancy of the water provides support and relieves stress and tension on the muscles and joint. The self-adjusting shields 22, 24 help to maintain the insulating efficiency of the chest. Thus, repeated treatments can be given with a minimal or limited amount of ice or fuel.

First aid, requiring wet heat or cold, can be provided by using the invention at construction sites, campsites, and remote locations. Paramedics can start treatments with the invention while on route to a hospital in cases involving burns, frostbite, swelling injuries, and some types of animal bites and stings. Visiting nurses and physical therapists can train home users to give self-treatments with the invention. Nursing homes, rehabilitation hospitals and other institutions could use the heater/cooler to treat patients in recreational settings including porches, patios, picnics and outings.

FIG. 6 indicates the position of a patient receiving a treatment of a lower leg. The opposite leg (not shown) can extend out over the top of the chest 4, resting on the chest lid. An arthritic patient might have both legs in the chest for treatment. The carrying handles are in an upright position for conveniently supporting a dinner tray 136 or table top. Thus, the patient can have dinner, write, or do other table activities.

Arms can be treated by placing the heater/cooler on a chair and inserting the arms through the limb ports.

In another application, the heater/cooler can be placed on a chair with the handles 126, 128 placed in the upright position. A large towel can then be supported over the handles to form a tent. A sitting patient can use the tent for inhalation treatments that require hot moist air (the vent port cover 118 and H/C source 46 are removed before the treatment). Medication that is appropriate for the ailment can be added to hot water in the chest 4.

OTHER EMBODIMENTS OF THE INVENTION

Second Embodiment

Figure 8:
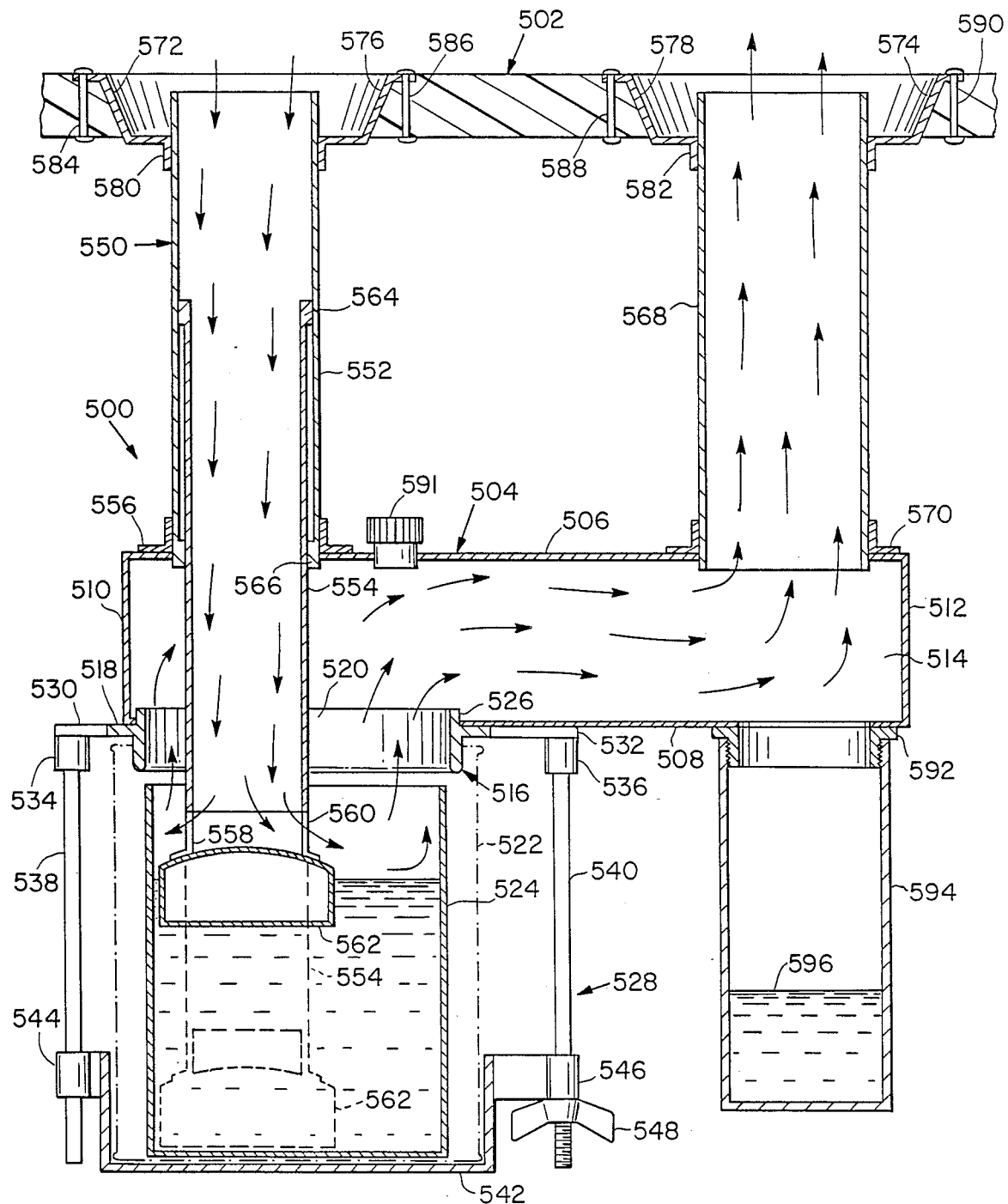
FIG. 8 is a cross-sectional view of a second embodiment of a submersible heating and cooling source taken along the axes of the conduits.

Shown in FIG. 8 is a H/C source 500 attached to a lid 502 of an insulated chest (not shown). The chest is similar to chest 4 shown in the first embodiment.

The H/C source 500 includes a transverse body 504 which is a six-sided rectangular box. Walls of the box include two rectangular horizontal walls which form a roof 506 and a floor 508. Connected around the horizontal walls are four vertical walls 510, 512, 514. The fourth vertical wall, opposite wall 514, is cut away to depict the cross-sectional figure and is therefor not shown.

An annular aperture through the floor 508 receives a cylindrical ring 516. The ring includes an annular flange 518 extending radially outward from a cylindrical portion 520. Ring 516 is welded to the floor 508 to form a fluid tight seal around the ring. An annular lower portion of ring 516 is shaped to be tightly received in the annular groove around the mouth of a conventional multi-friction can 522 (phantom image). Thus, ring 516 fits in place of a lid which is removed from the can. Multifriction cans are commonly used for containing paint and are available in several sizes.

Within can 522 is a fuel can 524 having a cylindrical wall which is spaced from the cylindrical wall of can 522. The inner can 524 contains semi-solid fuel. The double-wall arrangement prevents water, a combustion product, from condensing in the inner container. In this arrangement the fuel may be sold in can 524 which is inserted in can 522 by the user. Alternatively, the fuel may be sold enclosed by both cans which are disposable after use.

Combustion produced water that condenses in body 504 is prevented from entering the fuel can by an upper portion of ring 516 which forms an annular lip 526. The lip protrudes above the floor 508.

Ring 516 forms a fluid-tight seal with can 522 in the same manner as the lid of a multi-friction can. To insure that the can does not detach from the ring, a press assembly 528 is provided. The press assembly comprises a pair of lugs 530, 532 extending from diametrically opposite edges of flange 518. Fixedly attached to each lug is a respective bushing 534, 536. Each bushing having an aperture to receive a respective shaft 538, 540 fixed therein. The shafts are parallel with the axis of can 522.

A round shallow pan 542 receives a bottom portion of can 522. Extending from diametrically opposite edges of the pan are a pair of lugs fixed to respective bushings 544, 546. This set of bushings includes apertures for slidably receiving the shafts 538, 540 so that pan 542 is vertically movable on the shafts.

A lower end portion of shaft 540 has male threads which are threadedly mated with female threads of a wing nut 548.

Can 522, containing fuel can 524, can be mounted to H/C source 500 by two methods. One method is to hold the apparatus and press its ring 516 into the groove of can 522 as the can rests on a surface. Since the can will adhere to the ring, the pan may then be mounted and secured with the wing nut. The second method is to mount the pan containing the can 522 onto the shafts and to tighten the wing nut, thereby pressing the can onto the ring to form the seal.

An aperture in the roof 506 receives a first conduit 550 which comprises an upper cylindrical conduit 552 surrounding a lower cylindrical conduit 554. Both ends of the upper and lower conduits are open so that air can pass through the first conduit.

Upper conduit 552 is fixed to roof 506 by means of an annular pipe flange 556 encircling the conduit. The flange is welded to the conduit and roof so as to form a fluid tight seal around the conduit and flange.

Extending from the open lower end of conduit 554 are a pair of tines 558, 560. Each tine includes a lower portion bent into an L-shape which is welded to a hollow float 562. The float rests on the semi-solid fuel in can 524. The open lower end of conduit 554 is spaced from the float by the tines so that air passing down the first conduit can exit from the space between the tines. The air is spread at fuel level by a convex upper surface of the float to support combustion. The float rests partially submerged in the fuel and is supported by the buoyant force of the fuel.

Conduit 554 is slidably supported within conduit 552 so that the former is vertically movable between an upper position and a lower position. The lower position is indicated by the broken line image. As fuel is consumed by combustion, the conduit 554 follows the lowering fuel level thereby closely distributing airflow to the fuel. An outer annular lip 564 protrudes from the outside of an upper end portion of conduit 554. An inner annular lip 566 protrudes from the inside of a lower end portion of conduit 552. The inner and outer lips meet when conduit 554 is in the lower position. That prevents the lower conduit from falling out of the upper conduit when no fuel can is mounted.

A second aperture in roof 506 receives the lower end of a second cylindrical conduit 568. The second conduit is fixed to roof 506 by means of an annular pipe flange 570 encircling the conduit. Flange 570 is welded to the conduit and roof so as to form a fluid tight seal around the conduit and flange. Conduit 568 is open at both ends so that combustion gases can exit from the apparatus therethrough. The arrows in FIG. 8 show the direction of gaseous flow.

Upper end portions of conduits 550 and 568 are received into respective beveled annular vent ports 572, 574 in lid 502. The ports are simply round beveled apertures through the lid and are lined with conforming annular metal liners 576, 578 shaped like pie plates. Lower portions of the liners form annular pipe flanges 580, 582 which fixedly encircle the upper end portions of the conduits, respectfully. Rivets 584, 586, 588, 590 fix the liners in place.

Alternatively the H/C source 500 may be supported in an insulated chest by any of the support means described herein for other embodiments.

The fuel in the fuel can may be ignited by means of a lighting port 591 in roof 506. The lighting port is constructed similar to the lighting port of the first embodiment. Alternatively, the fuel may be ignited without lifting lid 502 by simply dropping a lighted paper match down conduit 550.

Welded around an edge defining an aperture through floor 508 is an externally threaded annular pipe flange 592. A hollow cylindrical water well 594 includes an internally threaded upper end portion so as to threadedly mate with the flange 592. The well 594 serves to collect water 596 that condenses within the body 504 and exhaust conduit 568 as result of combustion.

Third Embodiment

Figure 9:
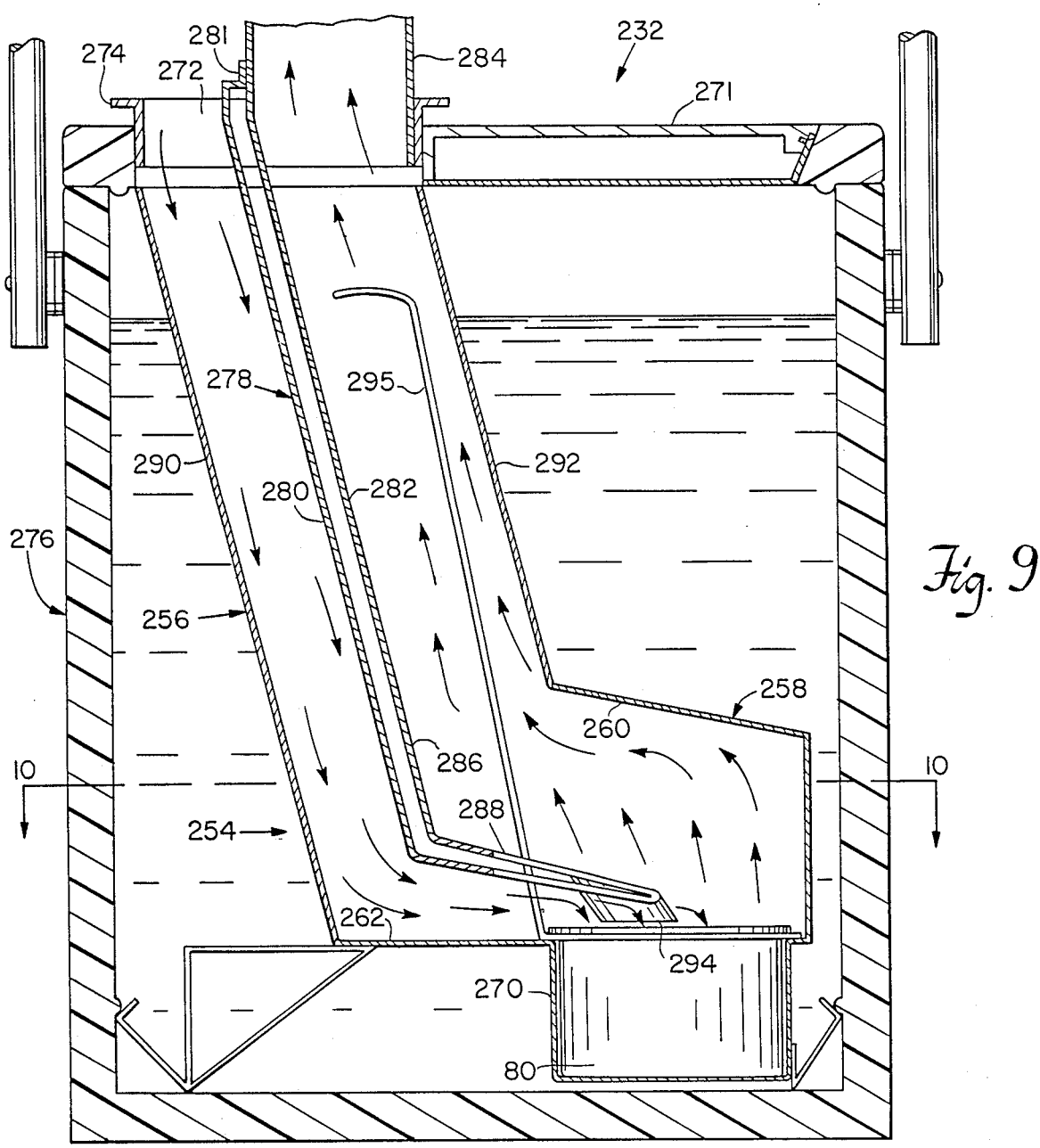
FIG. 9 is a cross-sectional view of a third embodiment of the invention taken along the axis of the conduit.
Figure 10:
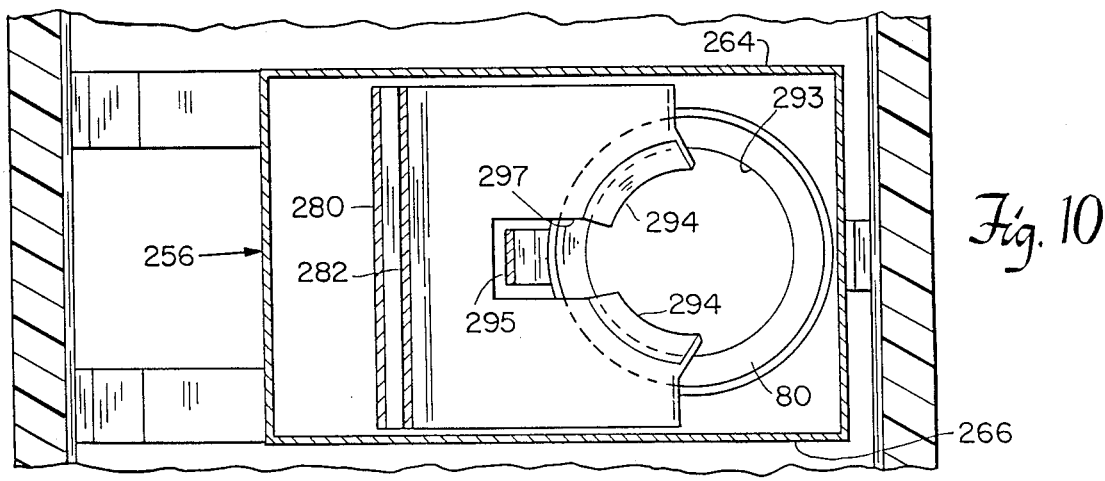
FIG. 10 is a fragmentary cross-sectional view of the embodiment of FIG. 9 taken along the line 10—10 of FIG. 9.

Shown in FIG. 9 and 10 is a heater/cooler 232 including a single conduit H/C source 254. A single conduit 256 is connected in fluid communication with a transverse body 258. As shown in FIG. 9, conduit 256 is inclined rather than vertical. The body 258 includes a roof 260 and a floor 262 which define respective upper and lower limits of a combustion chamber. Walls 264, 266 (FIG. 10) define lateral limits of the chamber. A fuel well 270, extending downward from the floor 262, receives a fuel can 80.

A square-shaped aperture in lid 271 receives a square-shaped open frame 272 having a retaining flange 274 extending peripherally from the frame. Flange 274 limits the extent to which the frame can pass through the lid aperture. As shown in FIG. 9, the lid aperture and the open frame are aligned with the upper end of conduit 256 for fluid communication between the interior of the conduit and the outside of container 276.

Within the open frame 272 and conduit 256 is a partition 278 comprising an outer wall 280 and an inner wall 282. The partition walls span between conduit and transverse body walls 264, 266. An upper portion of inner wall 282 forms one side of a four sided flue 284 which is welded to the frame 272. An upper end portion of the outer wall 280 is bent into an L-shape 281 which is welded to the flue. Lower end portions of both partition walls merge together and are connected at their lower ends.

As shown in FIG. 9, the lower end portions of the partition walls are bent at an angle in order to extend into the chamber of body 258. Hence, the partition comprises a conduit dividing portion 286 and a chamber dividing portion 288. Partition portion 286 divides the conduit 256 into an air route and a combustion gas route (which may be seen as first and second sub-conduits, respectively). The air route is defined by partition wall 280 and conduit wall 290. The combustion gas route is defined by partition wall 282 and conduit wall 292. Partition portion 288 partially divides the chamber into upper and lower sub-chambers.

Portion 288 includes an air gate or air director 294 extending downward toward the mouth 293 of fuel can 80 for directing a draft downward into the can. Director 294 is semi-circular in shape for distributing the airflow in a semi-circular pattern into the cylindrical can. The director is spaced from the can to allow room for the airflow. The portion 288 and its director also define a semi-circular passage for allowing combustion gases to rise from the fuel can and lower sub-chamber to the upper sub-chamber. The gases then pass into the combustion gas route of the conduit and out through the flue as shown by the arrows in FIG. 9. The inclined conduit causes rising hot gases in the combustion gas route to be urged away from the air route. Atmospheric air is drawn through open frame 272, down the air route of the conduit, and into the lower sub-chamber where it is directed downward into the fuel can.

Partition portion 288 also includes a cutout 297 to provide space for a fuel holding arm 295 so that the arm does not impede placement of the partition into the H/C source 254.

Fuel can 80 is removed by lifting flue 284, thereby removing frame 272 and partition 278 from the H/C source. Arm 295 is used to remove the fuel can. A new can of fuel is placed in the well before the assembly comprising the flue, partition, and frame, is replaced. Airflow into the fuel can may be adjusted by vertically adjusting frame 272 in the lid aperture, thereby adjusting the vertical position of the director relative to the can 80.

Fourth Embodiment

Figure 11:
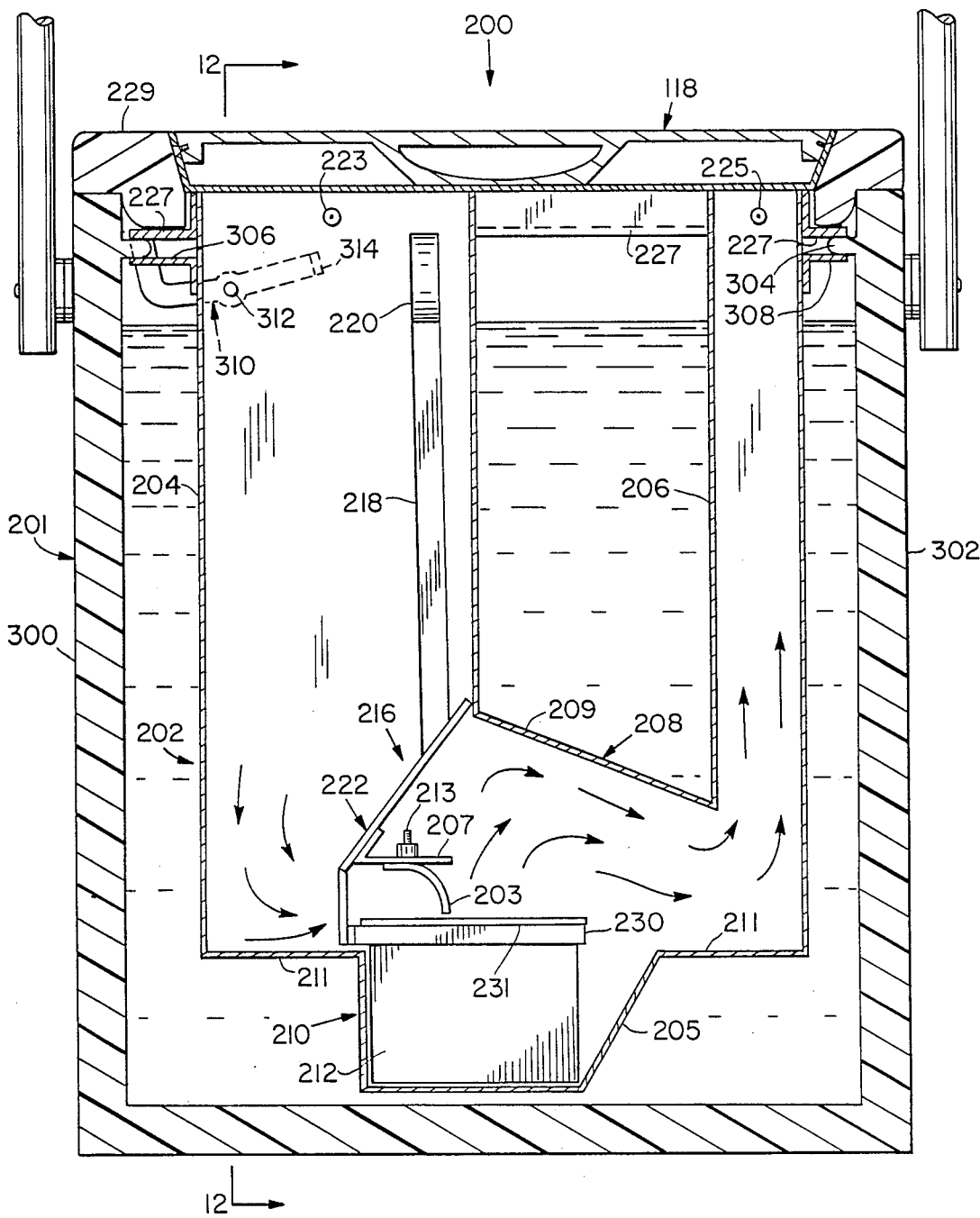
FIG. 11 is a cross-sectional view of a fourth embodiment of the invention taken along the axes of the conduits.
Figure 12:
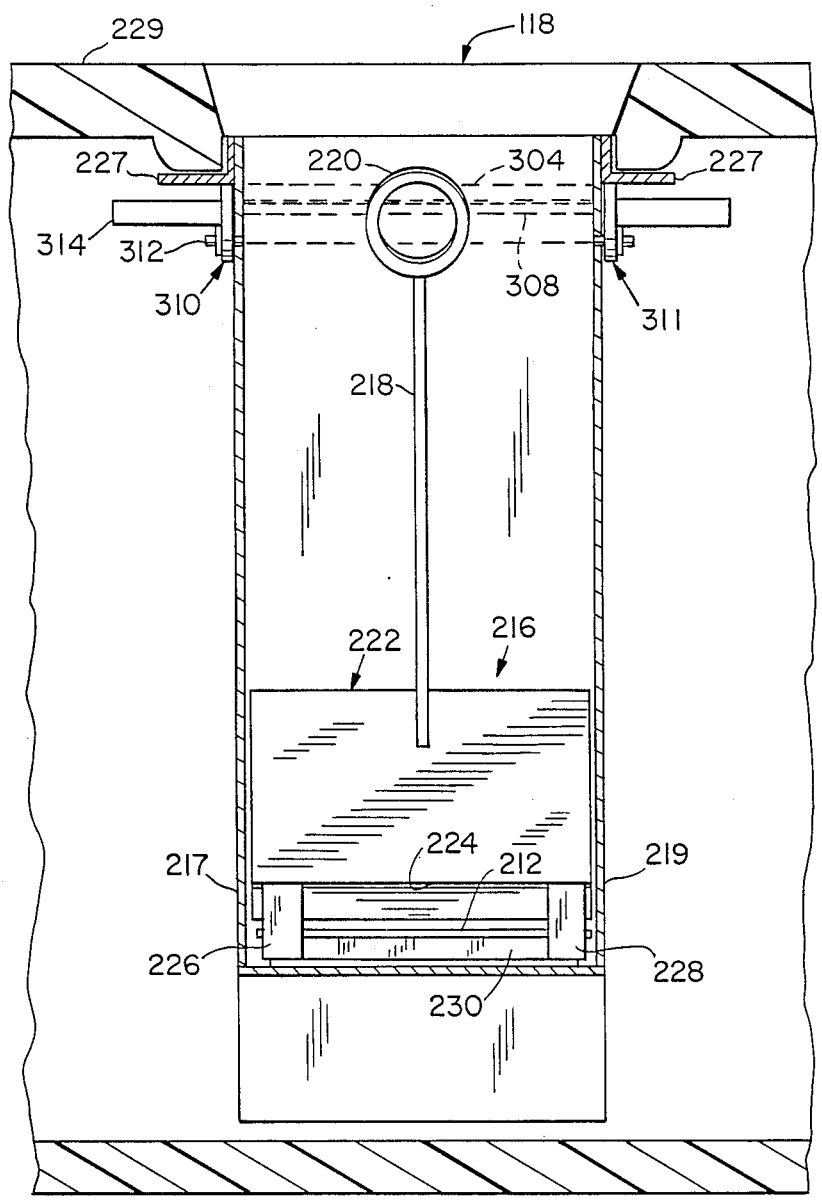
FIG. 12 is a fragmentary cross-sectional view of the embodiment of FIG. 11 taken along the line 12—12 of FIG. 11.

Shown in FIG. 11 and 12 is a versatile heater/cooler 200 similar to heater/cooler 2 of the first embodiment, but includes a modified H/C source 202.

H/C source 202 includes a first conduit 204 and a second conduit 206 in fluid communication with a transverse body 208. The conduits and body being essentially the same as respective corresponding components of H/C source 46 in the first embodiment. Walls which form a roof 209 and a floor 211 define respective upper and lower limits of a combustion chamber. Walls 217, 219 (FIG. 12) define lateral limits of the chamber. The joint between first conduit 204 and body 208 forms a first passage for fluid communication between the chamber and the first conduit interior. The joint between second conduit 206 and body 208 forms a second passage for fluid communication between the chamber and the second conduit interior. The height between the floor and the roof within the first passage of H/C source 202 is greater than the height within its second passage.

The fuel well 210 is comprised of five flat sides rather than being cylindrical. As can be determined from FIG. 11 and 12, the well is shaped in the form of a hollow truncated right prism.

The well receives a fuel can 212 which is shaped in the form of a rectangular solid rather than being cylindrical. An advantage is that more fuel may be held in a rectangular can having a same diameter as a cylindrical can. A top portion of can 212 defines an open mouth (not shown) leading to the interior of the can wherein the mouth is similar to mouth 293 of fuel can 80. The mouth could alternatively be square or rectangular.

Sloped side 205 forms a trough alongside the fuel can.

The conduits 204, 206, body 208, and well 210 form a Y-shaped device. The upper portion of the Y is formed by the conduits and the stem is formed by the well. The exterior surfaces of these elements, together with inner surfaces of the container 201, define a plurality of openings passing from one side of the Y to the other. Thus, the Y-shape enhances heat transfer because of its numerous hot surfaces and the openings defined by the same which promote convectional circulation of fluid through the openings. Since the Y-shape spans the interior of the container at a position perpendicular to the longitudinal axis of the container, convectional heating (and cooling) is especially effective. The beneficial Y-shaped configuration is also present in the first embodiment of the invention described herein.

A fuel holder/gate assembly 216 includes a shaft 218 having a ring-shaped handle 220. A lower end of the shaft is welded to a gate 222 which spans between lateral walls 217, 219 of the H/C source. The gate blocks an upper portion of the first passage. A lower portion of the gate defines a window 224 (FIG. 12) which is a space below the gate.

Also included in the gate is an adjustable air director 203 comprising a lower gate wall which is curved in a downward direction toward the mouth of the can. The director is movably supported by a bracket 207 which is welded to an upper wall of the gate. A screw 213, extending from the director, passes through an elongated slot (not shown) in the bracket wherein a nut mated to the screw holds the director to the underside of the bracket. The direction of the elongation of the slot is in the same transverse direction as the body 208. By loosening the nut, the director can be moved horizontally to adjust the amount of airflow into the fuel can, thereby controlling the rate of combustion.

The holder/gate assembly includes a pair of connectors 226, 228 (FIG. 12), extending downward from an edge of the upper wall of the gate. The connectors are fixed to a resilient U-shaped band 230 which tightly embraces the fuel can 212. The band is open ended (opening toward conduit 206) to receive the can. A lip 231 around an upper edge of the can prevents the same from slipping out of the band.

Hence, the assembly 216, comprising the handle 220, shaft 218, the gate assembly, connectors 226, 228, and band 230, form a unit. When the band holds a fuel can, the gate and fuel are connected in tandem so that they can be inserted (or removed from) within the H/C source 202 as a unit by way of the first conduit.

During combustion, the hot gases are guided downward by roof 209 toward the second conduit wherein they exit there-through. The downward slope of the roof enhances heat transfer to the liquid being heated. Air is drawn down the first conduit and through the window 224. The director over the mouth of the can, directs the air downward into the fuel can. The arrows in FIG. 11 indicate the direction of gaseous flow. As in other embodiments described herein, the vent port cover 118 must be removed for combustion to occur. In the figures where arrows indicate gas flow, it is understood that the vent port cover 118 must be removed for the gas flow to occur.

A seal flange 227 surrounds the upper end portions of both conduits. The seal flange is permanently fixed to the conduits with rivets 223, 225. An upper surface of the flange faces and meets flush with the undersurface of lid 229. As shown in the figures, the seal flange overlaps the lid edge defining a vent port which is similar to the vent port 110 of the first embodiment. When the lid is closed (on the container) and cover 118 is removed, the seal flange inhibits air from passing between the lid edge (the edge of the port) and the outside of the conduits. Opening (removing) the lid separates the same from the conduits and seal flange.

Each container wall 300 and 302 has a projection (including 304 on wall 302) protruding from an inner surface. Each wall projection being elongated in a direction parallel with the longitudinal axis of the container (perpendicular to the page of FIG. 11). The longitudinal dimension of each wall projection (indicated by broken lines in FIG. 12) is the same as the width of a conduit measured parallel to the mentioned axis.

Welded to each conduit is a lower flange 306, 308, respectively, wherein the lower flanges are positioned below and parallel to the seal flange. The longitudinal dimension of each lower flange (indicated by broken lines in FIG. 12) is the same as that of each wall projection so that each lower flange spans the width a conduit.

Each lower flange is spaced from the seal flange such that together they form a channel which receives a wall projection. Thus, the H/C source is supported, within the container, against the downward force of gravity and against the upward buoyant force of the liquid being heated in the container.

Pivotally supported on wall 217 of the first conduit is a latch 310. Support for the latch is provided by a pin 312 press fitted in a small aperture drilled through the conduit wall. The pin passes through an aperture in the latch wherein the latch pivots about the pin between an open position and a locked position. The latch is retained by a conventional retainer ring fitted in a groove around the pin. In the locked position, a distal end portion of the latch blocks an end of the channel formed by the flanges. Also, in the locked position, the distal end of the latch contacts the seal flange thereby preventing the latch from exceeding that position. The weight of a latch handle 314 urges the latch toward the locked position.

A similar latch 311 is mounted on the opposite wall 219 of the first conduit so that both ends of the channel are normally blocked by the two latches. Hence, the H/C source is prevented from sliding off of the wall projections when the container 201 is tipped or carried.

By pulling up on a latch handle, the H/C source can be removed or mounted from either end of the wall projections by sliding the H/C source longitudinally along the projections. During mounting, the latches will lock automatically when the H/C source is in its proper position.

Fifth Embodiment

Figure 13:
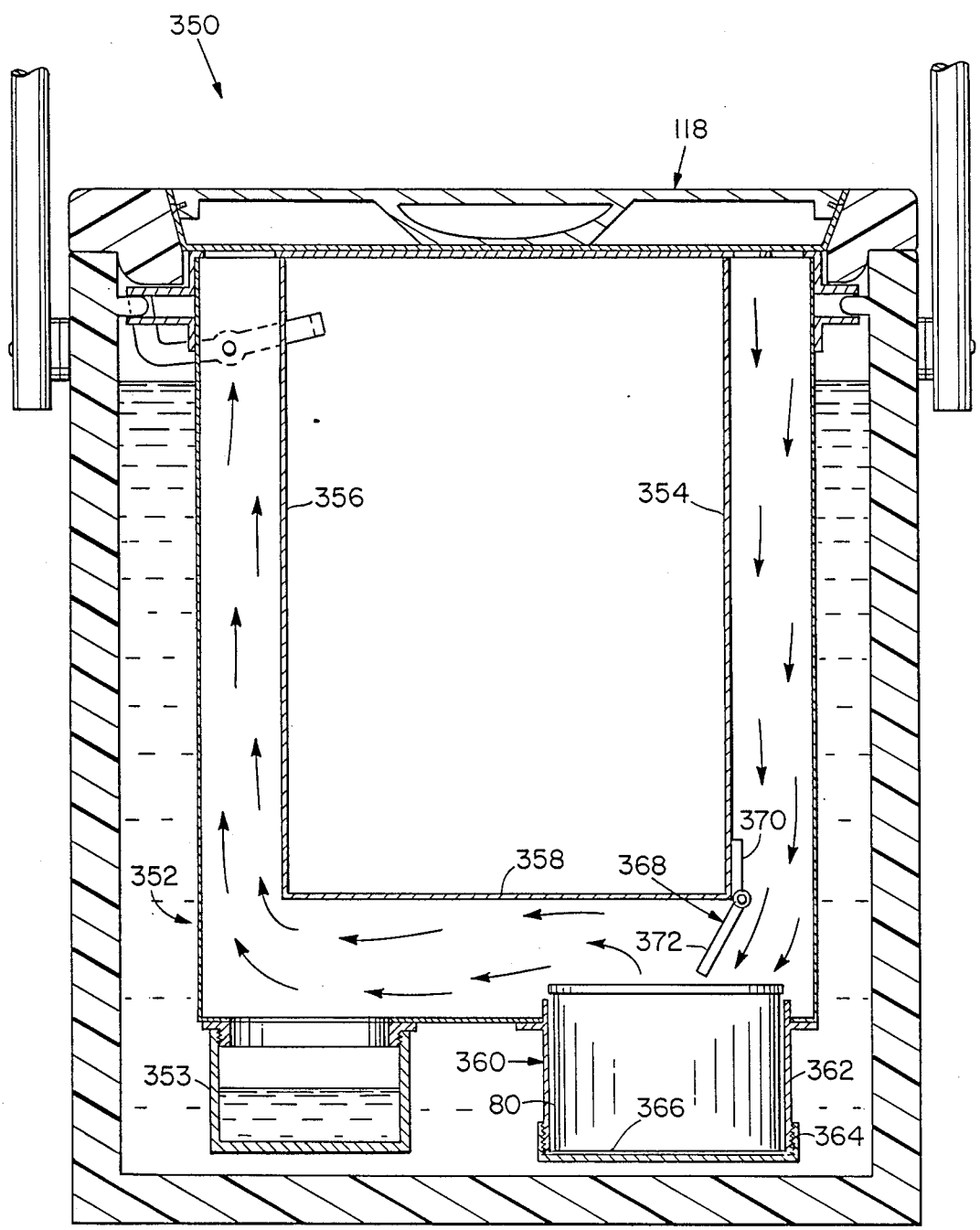
FIG. 13 is a cross-sectional view of a fifth embodiment of the invention taken along the axes of the conduits.

Shown in FIG. 13 is a heater/cooler 350 having a H/C source 352. The H/C source includes a first conduit 354 normally positioned vertically. Conduit 354 includes upper and lower end portions wherein the upper end portion is open for fluid communication between the hollow interior of the conduit and the outside atmosphere. Also included is a second conduit 356 normally positioned vertically. Conduit 356 includes upper and lower end portions wherein the upper end portion is open for fluid communication between the hollow interior of the conduit and the outside atmosphere.

A transverse body 358 defines a combustion chamber and is connected with the lower end portion of the first conduit 354 thereby forming a first passage between conduit 354 and the body. Thus, allowing fluid communication between the chamber and the first conduit interior. The body 358 is also connected with the lower end portion of the second conduit 356 thereby forming a second passage between conduit 356 and the body. Thus, allowing fluid communication between the chamber and the second conduit interior. The combination also allows the conduit interiors to be in fluid communication with each other.

Extending downwardly from the body 358 is a cup-shaped fuel well 360 in fluid communication with the conduits 354, 356. The well includes a hollow cylindrical portion 362 open at both ends and welded to the body 358. Also included is a screw-on base portion 364. The base portion is shaped like a round cake pan having a rim threaded on its inner side to mate with a threaded lower end of the cylindrical portion 362. The outer side of the base rim is knurled for gripping in order to tightly screw the base onto the cylindrical portion. A gasket 366 is included within the base to make a fluid tight seal with the cylinder. The gasket is heat resistant by being comprised of glass fibers. A soft metal gasket could also be used.

Removal of the base provides a means for inserting a fuel can 80 through the open lower end of the cylindrical portion wherein the base is then replaced.

Also included within H/C source 352 is a movable air director or gate 368 constructed like a door hinge. The gate comprises a fixed wall 370 welded to an inside surface of conduit 354 and a movable wall 372 connected to the fixed wall by a pinned joint. The joint being tight so that the movable wall remains in a position set by a user. Access to the gate (by a user) is through the well when the base 364 and fuel can 80 are removed so that the gate can be adjusted as preferred. The movable wall 372 is normally directed downward toward the open mouth of the fuel can.

Like the gate of H/C source 202, gate 368 spans between the vertical walls of the first passage to substantially block the same. During combustion the draft passes down the first conduit 354 and is directed downward into the fuel can. Combustion gases emerge on the opposite side of the gate and pass through the chamber to leave through the second conduit 356. The arrows in FIG. 13 indicate the direction of gaseous flow.

Connected below an aperture in the floor of transverse body 358 is a detachable water well 353. The water well is constructed in substantially the same manner as the water well of the second embodiment.

It is understood that modifications having multiple fuel cans in a single fuel well or multiple wells and fuel cans may be incorporated in any of the embodiments described herein.

While the above description contains many specificities, these should not be construed as limitations on the scope of the invention, but rather as exemplifications of preferred embodiments thereof. Those skilled in the art will envision other possible variations that are within its scope. Accordingly, the scope of the invention should be determined not by the embodiments illustrated, but by the appended claims and their legal equivalents.

What is claimed is:

1. A heater for heating liquid comprising:
   a first conduit having a hollow interior and upper and lower end portions wherein the upper end portion includes an opening for fluid communication between the conduit interior and the outside atmosphere;
   a second conduit having a hollow interior and upper and lower end portions wherein the upper end portion includes an opening for fluid communication between the second conduit interior and the outside atmosphere; and
   a body defining at least a portion of a combustion chamber, the body being connected with the lower end portions of the first and second conduits such that the chamber is in fluid communication with the interiors of the conduits, the body having a roof for transferring heat to a liquid environment in which the body can be submerged, the roof having an underside positioned directly over the chamber wherein the underside is sloped to extend in a downward direction to a lateral portion of the chamber and generally downward toward the second conduit, the body having a floor below the rood, the roof underside being generally sloped upward toward the first conduit such that the vertical distance within the chamber between the floor and the roof generally increases as the distance toward the first conduit decreases.

2. The heater as defined in claim 1, wherein a cross-sectional area taken perpendicularly through a longitudinal axis of the first conduit is substantially larger than a cross-sectional area taken perpendicularly through a longitudinal axis of the second conduit wherein the relatively large first conduit area connecting with the highest portion of the chamber enables convenient entry of relatively large combustion related components into the chamber by way of the first conduit.

3. The heater as defined in claim 1, further comprising a gate which spans across the lower interior of the heater to guide air downward close to the floor of the chamber for efficient combustion, the gate being removable by way of the first conduit.

4. The heater as defined in claim 1, further comprising an air director spanning the lower interior of the heater, the director having a curved wall for directing the air downward to enhance combustion, the director being removable by way of the first conduit.

5. A portable combustion apparatus comprising:
   a container for containing liquid, the container having walls which includes an inside surface;
   a heater for heating liquid, the heater having a hollow conduit including an outside surface and upper and lower end portions wherein the upper end portion includes an opening for fluid communication between the conduit interior and the outside atmosphere, the heater having connecting means for connecting a fuel source in fluid communication with the interior of the conduit for supporting combustion of fuel when the heater is at least partially submersed in the liquid for heating the same;
   an elongated projection fixed to one said surface; and
   a channel having an end portion, the channel being fixed to said other surface and the channel receiving the projection through the end portion such that the channel and projection are slidable relative to each other so that the heater can be detachably mounted to the interior of the container wherein the heater is held against the upward buoyant force of the liquid and the downward force of gravity.

6. The portable combustion apparatus as defined in claim 5, wherein the channel and elongated projection are normally horizontal.

7. The portable combustion apparatus as defined in claim 5, further comprising:
   the container having a lid, the lid having an edge portion defining a vent port;
   the channel forming at least a portion of a flange, the flange substantially surrounding the conduit and being normally positioned beneath and adjacent the lid edge portion when the lid is on the container so that the flange inhibits the passage of gases other than those associated with combustion from passing through the vent port thereby inhibiting heat losses form the container.

8. The portable combustion apparatus as defined in claim 5, further comprising a latch supported to move between an open position and a locked position, the latch in the locked position blocks the end of the channel thereby securing the heater within the container.

9. The portable combustion apparatus as defined in claim 8, wherein the latch includes a handle which is weighted such that the latch is urged toward the locked position by gravity.

10. A portable combustion apparatus comprising:

a conduit having a hollow interior and upper and lower end portions wherein the upper end portion includes an opening for fluid communication between the conduit interior and the outside atmosphere;

connecting means for connecting a fuel source in fluid communication with the interior of the conduit for supporting combustion of the fuel;

a container having a plurality of walls enclosing the conduit and connecting means, the container having an opening for allowing fluid communication between the conduit interior and the exterior of the container; and an openable cover positioned across the container opening thereby inhibiting the passage of air therethrough, the cover having a bottom surface positioned at the conduit opening for blocking the same thereby preventing combustion of fuel.

11. The apparatus as defined in claim 10, wherein the container opening is a vent port defined by an openable lid which forms an upper wall of the container.

* * * * *